US008459131B2

(12) United States Patent
Anderson

(10) Patent No.: US 8,459,131 B2
(45) Date of Patent: Jun. 11, 2013

(54) SOIL SAMPLING MACHINE AND METHOD OF USE

(75) Inventor: Mark W. Anderson, Aspers, PA (US)

(73) Assignee: GVM, Inc., Biglerville, PA (US)

( * ) Notice: Subject to any disclaimer, the term of this patent is extended or adjusted under 35 U.S.C. 154(b) by 82 days.

(21) Appl. No.: 13/168,429

(22) Filed: Jun. 24, 2011

(65) Prior Publication Data

US 2011/0314938 A1    Dec. 29, 2011

Related U.S. Application Data

(60) Provisional application No. 61/358,840, filed on Jun. 25, 2010.

(51) Int. Cl.
*G01N 1/04* (2006.01)
(52) U.S. Cl.
USPC ........................................................ 73/864.44
(58) Field of Classification Search
None
See application file for complete search history.

(56) References Cited

U.S. PATENT DOCUMENTS

| 5,950,741 | A | * | 9/1999 | Wright et al. ................... 175/20 |
| 7,255,016 | B2 | | 8/2007 | Burton |
| 7,552,654 | B2 | | 6/2009 | Burton |
| 7,575,069 | B2 | * | 8/2009 | Pavlik ............................ 175/20 |
| 2010/0037712 | A1 | | 2/2010 | Burton |
| 2012/0010788 | A1 | | 1/2012 | Dearborn et al. |

OTHER PUBLICATIONS

Paul Schrimpf, Jimmy Sanders: Technology in Overdrive, HTTP://www.croplife.com/article/1606, May 7, 2009, 3 pages.
AgRobotics AutoProbe Demo at CTIC Tour, HTTP://precisionpays.com/?s=auto+probe&x=130&y=10, Aug. 28, 2011, 2 pages.
Joe Russo, Data Management Tools, InfoAg 2007, Jul. 10, 2007, 61 pages.

* cited by examiner

*Primary Examiner* — Robert R Raevis
(74) *Attorney, Agent, or Firm* — McNees Wallace & Nurick LLC

(57) ABSTRACT

A soil sampling machine and its method of use is provided. The soil sampling machine can include a sampling mechanism configured and positioned to obtain a soil sample. A storage tank is located on the machine and can store the obtained sample material from the sampling mechanism. A hose connects the sampling mechanism and the storage tank and a vacuum generator generates a vacuum force in the hose to transport the obtained soil sample from the sampling mechanism to the storage tank.

18 Claims, 8 Drawing Sheets

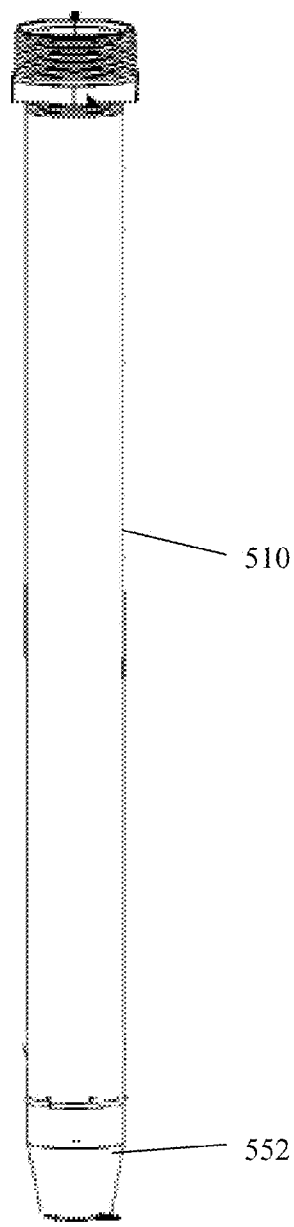 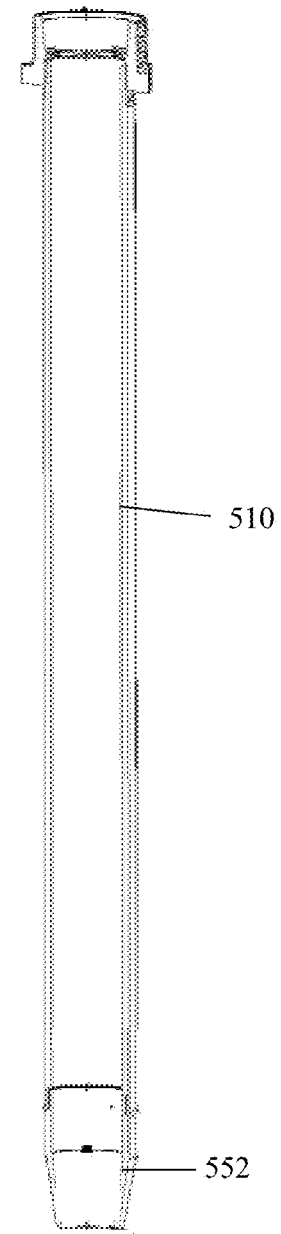
FIG. 12          FIG. 13

SOIL SAMPLING MACHINE AND METHOD OF USE

CROSS-REFERENCE TO RELATED APPLICATIONS

This application claims the benefit of U.S. Provisional Application No. 61/358,840, entitled "SOIL SAMPLING SYSTEM AND METHOD," filed Jun. 25, 2010, which application is hereby incorporated by reference in its entirety.

BACKGROUND

The application generally relates to the taking of soil samples. The application relates more specifically to a machine for acquiring soil samples in an agricultural field and the method of using the machine to acquire the soil samples.

The taking or acquiring of soil samples from an agricultural field and the subsequent analysis of the soil samples can be useful in increasing the crop yield for that agricultural field. However, the acquisition of soil samples has been a manually performed process that is difficult and time consuming. To take a soil sample, a person had to manually insert a probe into the ground to remove the soil or sample material from the ground, and then store and label the sample material from the probe for subsequent analysis. Another option for taking the soil sample was to use an all terrain vehicle (ATV) equipped with a device to insert the probe into the ground. However, due to the limited capabilities of the ATV, the device mounted on the ATV could not provide much additional insertion force over the insertion force that could be provided by the person. Further, if the amount of sample material removed from the ground was not a sufficient sample for analysis, additional sample material had to be removed from the ground until a sufficient sample had been obtained. The process is then repeated at the next soil sample location in the agricultural field, which can have numerous sampling points or locations depending on the size of the agricultural field. Thus, depending on the number of sampling locations in an agricultural field, a person could spend a day or more collecting the necessary soil samples from an agricultural field.

Therefore, what is needed is a machine and method that can simplify and reduce the time needed for the soil sampling process.

SUMMARY

The present application is directed to a method of obtaining a soil sample from an agricultural field. The method includes acquiring sample material from an agricultural field with a sampling mechanism mounted on a soil sampling machine and transferring the acquired sample material from the sampling mechanism to a storage tank located on the soil sampling machine with a vacuum force. The method also includes removing the acquired sample material from the storage tank and placing the acquired sample material in a container.

The present application is additionally directed to a soil sampling machine. The soil sampling machine includes a sampling mechanism configured and positioned to obtain a soil sample and a storage tank to store an obtained soil sample from the sampling mechanism. The soil sampling machine also includes a hose connecting the sampling mechanism and the storage tank and a vacuum generator to generate a vacuum force to transport the soil sample from the sampling mechanism to the storage tank.

One advantage of the present application is the automation of the soil sampling process.

Another advantage of the present application is that the sampling process is more consistent and repeatable.

Still another advantage of the present application is the ability to sample an increased number of acres per hour compared to manual sampling.

A further advantage of the present application is increased efficiency in collecting samples.

Other features and advantages of the present application will be apparent from the following more detailed description of the preferred embodiment, taken in conjunction with the accompanying drawings which illustrate, by way of example, the principles of the application.

BRIEF DESCRIPTION OF THE DRAWINGS

FIG. 12 shows a front view of the probe of FIG. 5.

FIG. 13 shows a cross-sectional view of the probe of FIG. 12.

Wherever possible, the same reference numbers are used throughout the drawings to refer to the same or like parts.

DETAILED DESCRIPTION OF THE EXEMPLARY EMBODIMENTS

Figure 1:
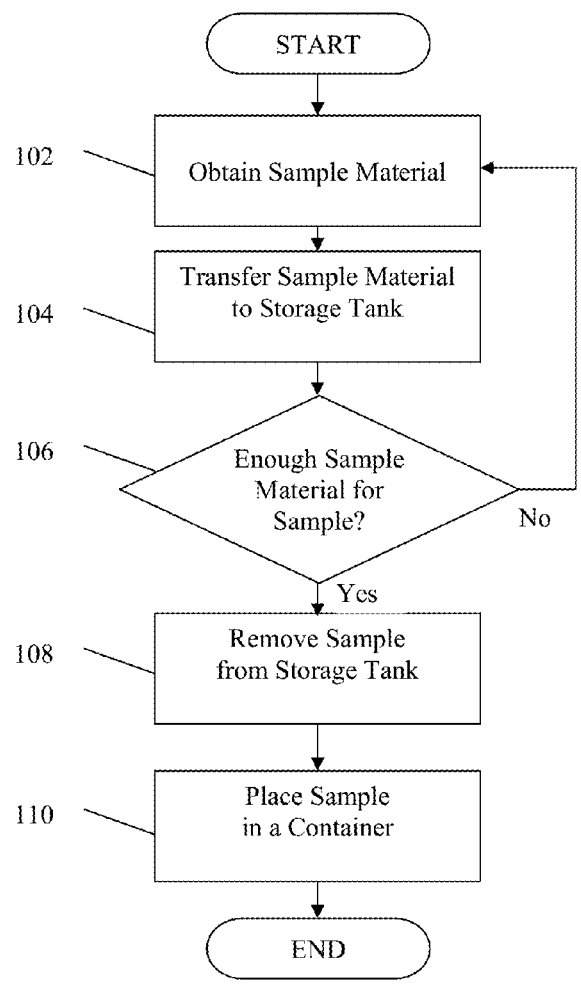
FIG. 1 shows a flowchart of an exemplary embodiment of the process for acquiring soil samples from an agricultural field.

FIG. 1 shows an embodiment of the process for acquiring soil samples using a soil sampling machine. The process begins by obtaining sample material, e.g., soil or dirt, from the ground using the soil sampling machine (step 102). The sample material can be obtained from the ground using a probe(s), auger or other similar sampling device. If the sample material is to be obtained using a probe(s), the probe(s) can be inserted into the ground by the soil sampling machine (see e.g., FIG. 2) to acquire the sample material and then can be subsequently removed from the ground with the sample material. Alternatively, if the sample material is to be obtained using an auger, the rotating auger can be inserted into the ground by the soil sampling machine to obtain and transport the sample material from the ground.

In one exemplary embodiment, multiple probes can be used to acquire sample material. The number of probes that can be used to obtain enough sample material for a sufficient sample can be based on the measurement depth, i.e., the distance the probe is inserted into the ground, for the corresponding probes and the internal diameter of the probes. If the measurement depth used for the probe(s) does not provide enough sample material for a sufficient sample, then the probe(s) may have to be reinserted into the ground until enough sample material has been obtained. The amount of sample material or soil needed for a sufficient sample can vary based on the analysis to be performed, the type of soil or sample material, and other factors.

After the sample material has been obtained, the sample material can be transferred or transported to a storage tank or container located on the soil sampling machine (step 104). A hose, tube or conduit can interconnect the probe(s) or auger and the storage tank and a vacuum force can be used to move or transport the sample material through the hose from the probe(s) or auger to the storage tank. In one embodiment, the hose or conduit can be clear to permit the operator of the soil sampling machine to visually confirm the transfer of the sample material to the storage tank. If the sample material is obtained using a single probe, the hose can be attached directly to the probe or the hose can be connected to a multiple branch pipe or hose, e.g., a "Y" pipe, or to a header or storage vessel interconnecting the probes if several probes are used. In another embodiment, if multiple probes are used, each probe could have its own hose connected to the storage tank to permit the vacuum force to be applied to each probe and hose individually. To transfer the sample material from the probe(s) to the storage tank, the vacuum force can be engaged after the probe is removed from the ground. The probe(s) can then be rotated into a substantially horizontal position (see e.g., FIG. 3) and a vibrator or vibrating device can be started to remove or loosen the material from the probes. After a predetermined time period has elapsed, the vibrator and vacuum force can be disengaged. In one embodiment, if the sample material is loose or sandy soil, the vacuum force can be engaged as the probe is being withdrawn from the ground to prevent the sample material from flowing out of the probe and onto the ground.

Alternatively, if the sample material is to be obtained using an auger, the hose can be connected to a storage area in proximity to the auger that receives the sample material from the auger. To transfer the sample material from the auger to the storage tank, the vacuum force can be engaged at the same time (or shortly thereafter) as the auger is engaged and the vacuum force can continue to operate during the operation of the auger and for a predetermined time period after auger operation has ceased. Alternatively, the sample material from the auger can be stored in the storage area associated with the auger for the duration of auger operation and then transferred to the storage tank in a similar manner as described above for the probes once auger operation has stopped.

After the sample material has been transferred to the storage tank, a determination is made on whether enough sample material has been obtained for a sufficient sample (step 106). If there is not enough sample material for a sufficient sample, the process returns to step 102 to obtain additional sample material. In one embodiment, as each additional sample is taken or acquired, the sample material from that sample can be mixed with the stored sample material from previously taken samples by the vacuum force that is present in the storage tank. Otherwise, the process proceeds to remove the sample material from the storage tank (step 108) and place the soil sample in a container (step 110). To remove the sample material from the storage tank, the storage tank and any associated filtration systems can be vibrated to loosen or remove the sample material from the storage tank. A valve or gate, e.g., a butterfly valve, associated with the storage tank is opened and the sample material is dispensed onto a conveyor or auger by force of gravity and the vibration of the storage tank. The conveyor or auger can then transport the sample material into the cab of the soil sampling machine. Once the sample material has reached the cab of the soil sampling machine, the operator of the soil sampling machine can place the sample material in a container, such as a bag, and provide an appropriate label for the container. In another embodiment, the operator of the soil sampling machine can transfer the sample material directly from the storage tank to the container.

Figure 2:
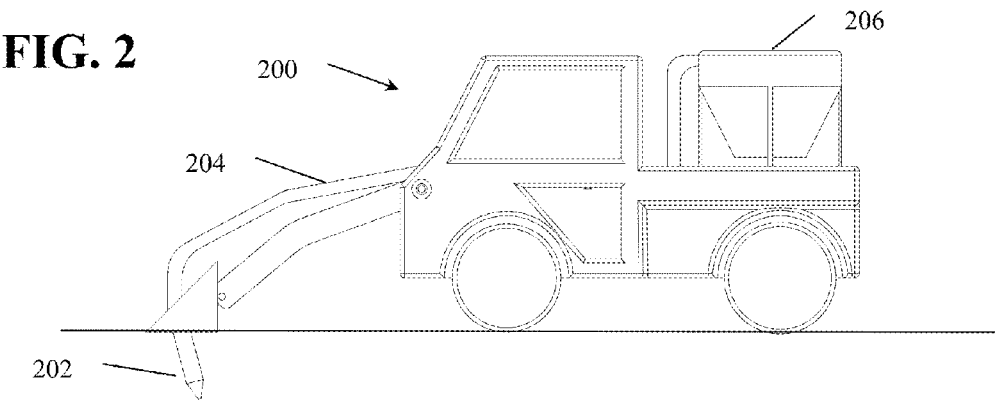
FIGS. 2-4 show different views of an exemplary embodiment of a machine for acquiring soil samples.
Figure 3:
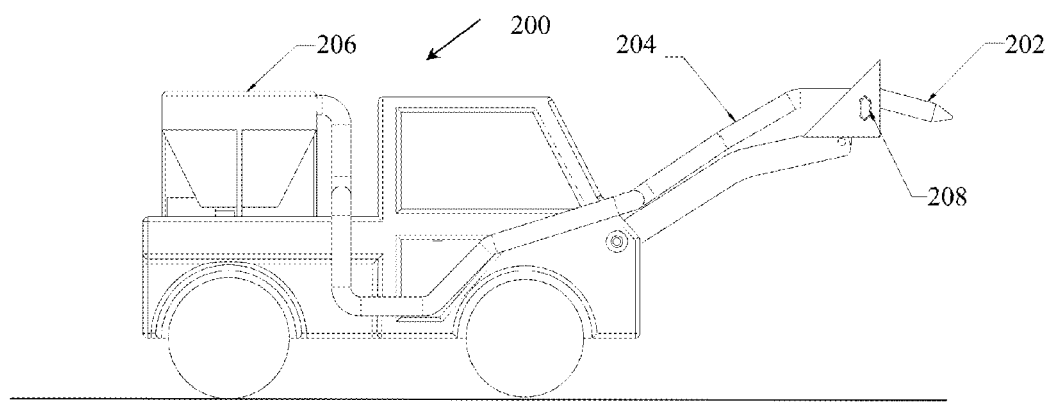
Figure 4:
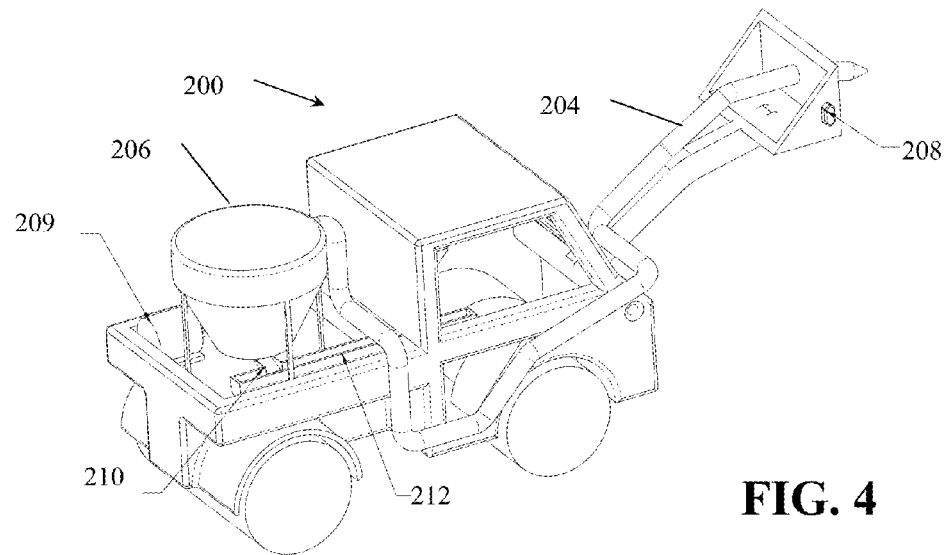

FIGS. 2-4 show one embodiment of a soil sampling machine. In FIG. 2, a soil sampling machine 200 can be taking or acquiring sample material with the probe 202. In the embodiment shown in FIG. 2, the probe(s) can be inserted into the ground at the angle of rotation of the mast. In FIG. 3, the soil sampling machine 200 can be positioned to transfer or transport the sample material from the probe 202 to the storage tank 206 through the hose 204 using a vacuum force. A vibrator 208 can be used to loosen or remove the material from the probe 202 for transport through the hose 204. In FIG. 4, the sample material can be transferred or transported from the storage tank 206 to the cab of the soil sampling machine 200. A valve or gate 210 can be used to permit the sample material to flow or travel from the storage tank 206 to a conveyor or auger 212 to take or transport the sample material to the cab of the soil sampling machine 200. A hydraulic generator 209 and possibly one or more transformers can be used to provide the necessary power to generate the vacuum force to transport the sample material through the hose 204, to operate the vibrator 208 and any vibrator used with the storage tank 206, to actuate the valve 210 and to operate the conveyor 212. In another embodiment, other types of generators, such as a diesel or gasoline generators or electric generators, can be used to power the components.

Figure 5:
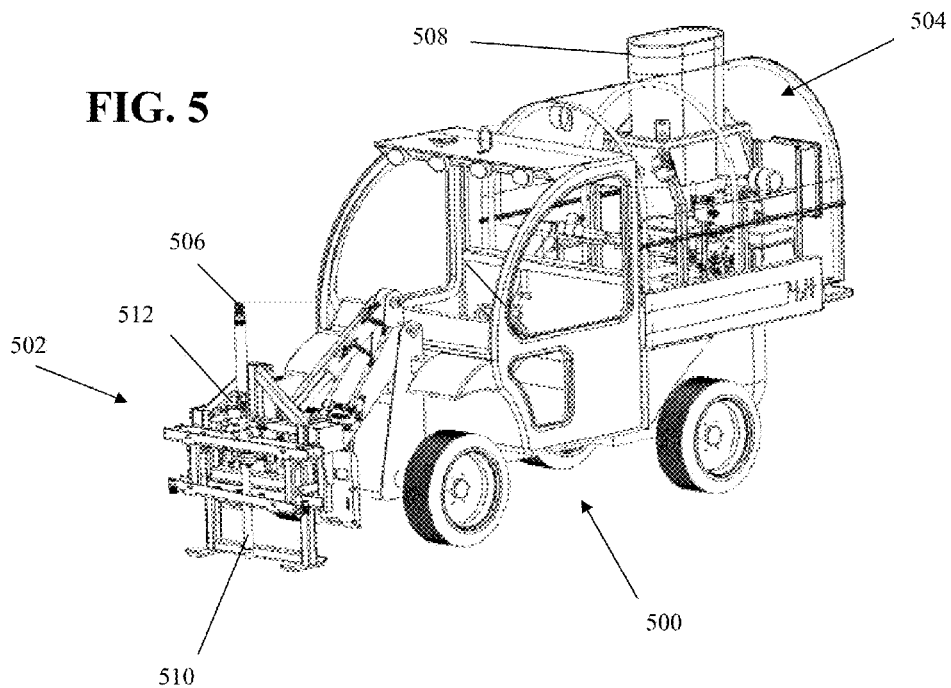
FIG. 5 shows another exemplary embodiment of a machine for acquiring soil samples.

FIG. 5 shows an exemplary embodiment of a soil sampling machine. The soil sampling machine 500 can have a sampling mechanism 502 located at the front of the machine 500 and a sample handling system 504 located at the rear of the machine 500. A hose or tube (not shown) can connect a connection point 506 of the sampling mechanism 502 to a storage tank or vacuum silo 508 of the sample handling system 504. The sampling mechanism 502 can use a single probe 510 to obtain sample material and a vibrator or vibrational device 512 can be used to loosen the sample material from the probe 510 for subsequent transport through the tube to the storage tank 508. The sample handling system 504 can include a vacuum generator to generate a vacuum force to transport the sample material from the sampling mechanism 502 through the tube to the storage tank 508.

Figure 6:
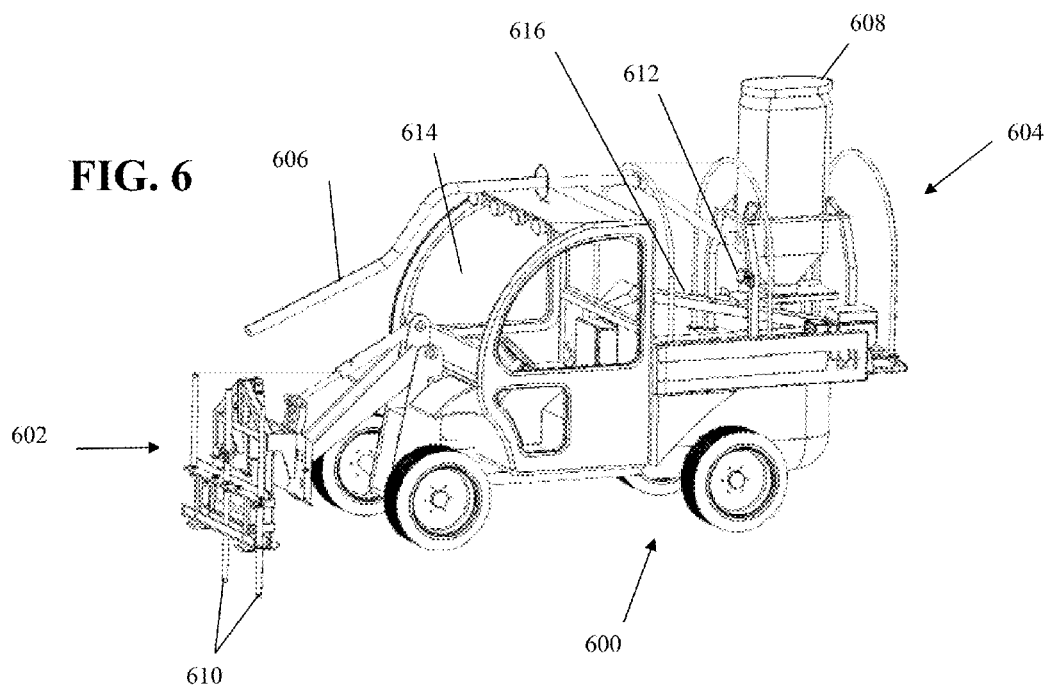
FIG. 6 shows still another exemplary embodiment of a machine for acquiring soil samples.

FIG. 6 shows another exemplary embodiment of a soil sampling machine. The soil sampling machine 600 can have a sampling mechanism 602 located at the front of the machine 600 and a sample handling system 604 located at the rear of the machine 600. The sampling mechanism 602 can use multiple probes 610 to obtain sample material. A hose or tube 606 (partially shown) can connect one or more connection points of the sampling mechanism 602 to a storage tank or vacuum silo 608 of the sample handling system 604. Depending on the multiple probe configuration used, the hose or tube 606 may incorporate manifolds and/or valves to regulate the vacuum force and the transporting of the sample material. The sample handling system 604 can include a vibrator or vibrational device 612 to loosen sample material stored in the storage tank 608 for transport to the cab 614 of the soil sampling machine by a conveyor 616.

Figure 7:
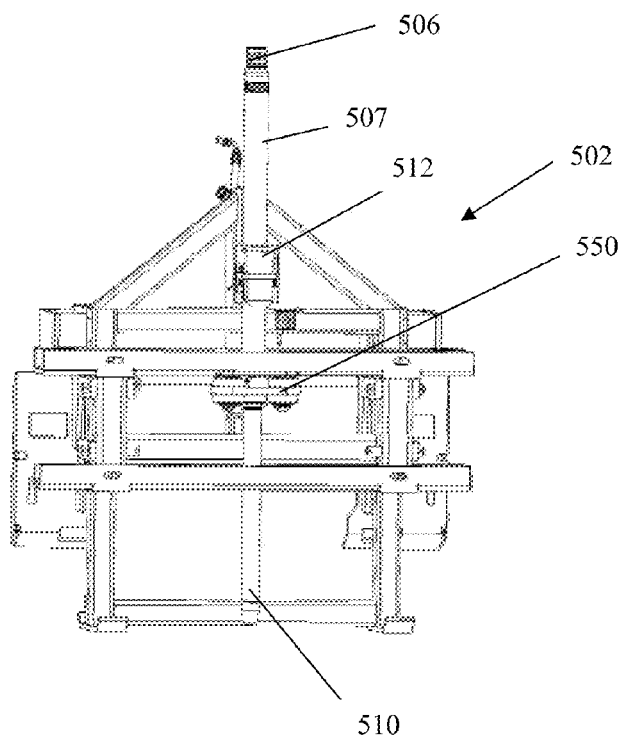
FIGS. 7 and 8 show front and rear views of the sampling mechanism of FIG. 5.
Figure 8:
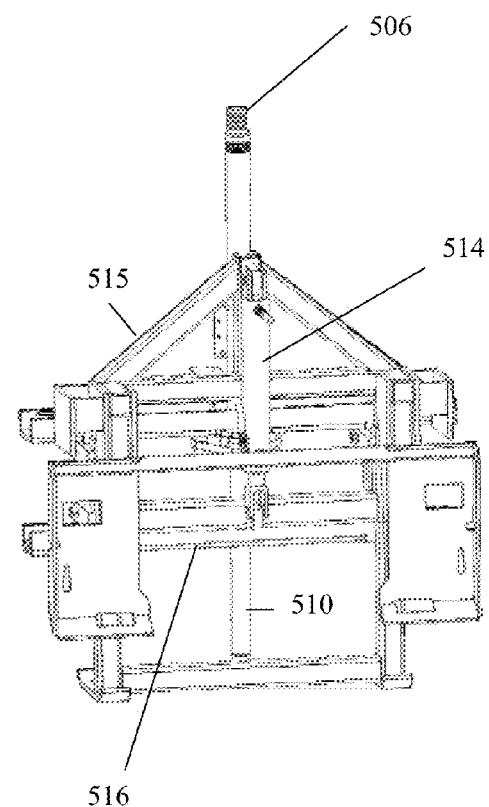

FIGS. 7 and 8 show the sampling mechanism of FIG. 5. The sampling mechanism 502 can be mounted to the soil sampling machine 500 by hydraulic cylinders other suitable connection techniques. The sampling mechanism 502 can include a cylinder 507 having the connection point 506 for the hose. The cylinder 507 can be connected to the probe 510 and when vibrator 512 is operated, the sample material is loosened or removed from the probe 510 and travels through the cylinder 507 to the connection point 506 for subsequent travel through the hose. An isolator(s) 550 can be mounted on a frame 515 to limit or prevent the transfer of the vibrational force from the vibrator 512 to the frame 515 and/or other components of the sampling mechanism 502. The isolator(s) 550 can be used to maintain the vibrational force from the vibrator 512 on just the probe 510 and cylinder 507.

The sampling mechanism 502 can also include a hydraulic cylinder 514 mounted on the frame 515 to move a sliding mechanism 516 to which the probe 510 is connected. To acquire sample material with the probe 510, the sampling mechanism 502 is placed on the ground by the soil sampling machine 500. Once the sampling mechanism 502 is in the proper position, the hydraulic cylinder 514 is actuated to move or lower the sliding mechanism 516 along the frame 515 and force the probe 510 into the ground to acquire the sample material. In one exemplary embodiment, the hydraulic cylinder 514 can insert the probe 510 into the ground with a force of between about 2500 psi and about 3000 psi. The insertion force applied to the probe 510 can be varied based on the selection and configuration of the hydraulic cylinder 514 and sliding mechanism 516. To remove the probe 510 from the ground, the hydraulic cylinder 514 is actuated in the opposite direction to move or raise the sliding mechanism 516 and the probe 510. The movement of the sliding mechanism 516 as well as the configuration of the probe 510 can be used to determine the measurement depth for the probe 510. In another embodiment, pneumatic cylinders could be used instead of the hydraulic cylinders. In still another embodiment, a probe can be used having a length greater than or equal to the maximum desired measurement depth and a linear actuator can be used to control the insertion of the probe to obtain any desired measurement depth up to the maximum measurement depth. Thus, a single probe can be used to take samples of different measurement depths.

Figure 14:
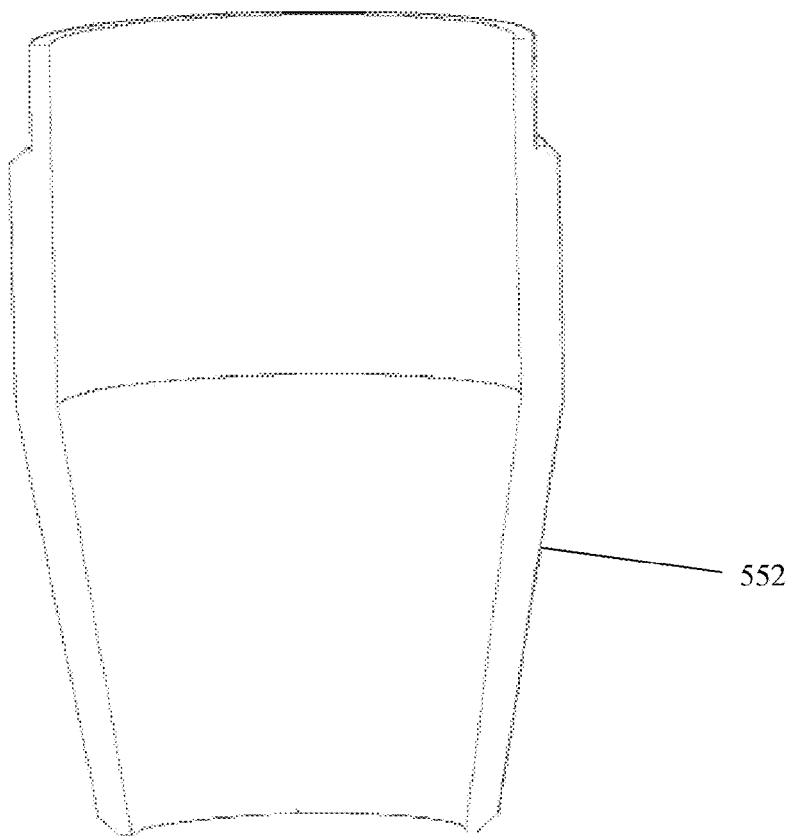
FIG. 14 shows an enlarged view of the tip of the probe of FIG. 13.

FIGS. 12-14 show an exemplary embodiment of a probe that can be used with the sampling mechanism. Probe 510 can have a tip or end portion 552 that can be inserted into the ground. As can be seen in FIG. 14, one end of the tip 552, i.e., the end that is initially inserted into the ground, can have a first internal diameter and the opposite end of the tip 552, i.e., the end that mates or connects with the rest of the probe 510, can have a second internal diameter that is greater than the first internal diameter. The change in the internal diameter of the tip 552 can permit the sample material entering the probe 510 to expand or decompress in order to enable the vacuum force to transport the material from the probe 510 to the storage tank 508. In one exemplary embodiment, the first internal diameter can be 1.16 inches and the second internal diameter can be 1.61 inches.

Figure 9:
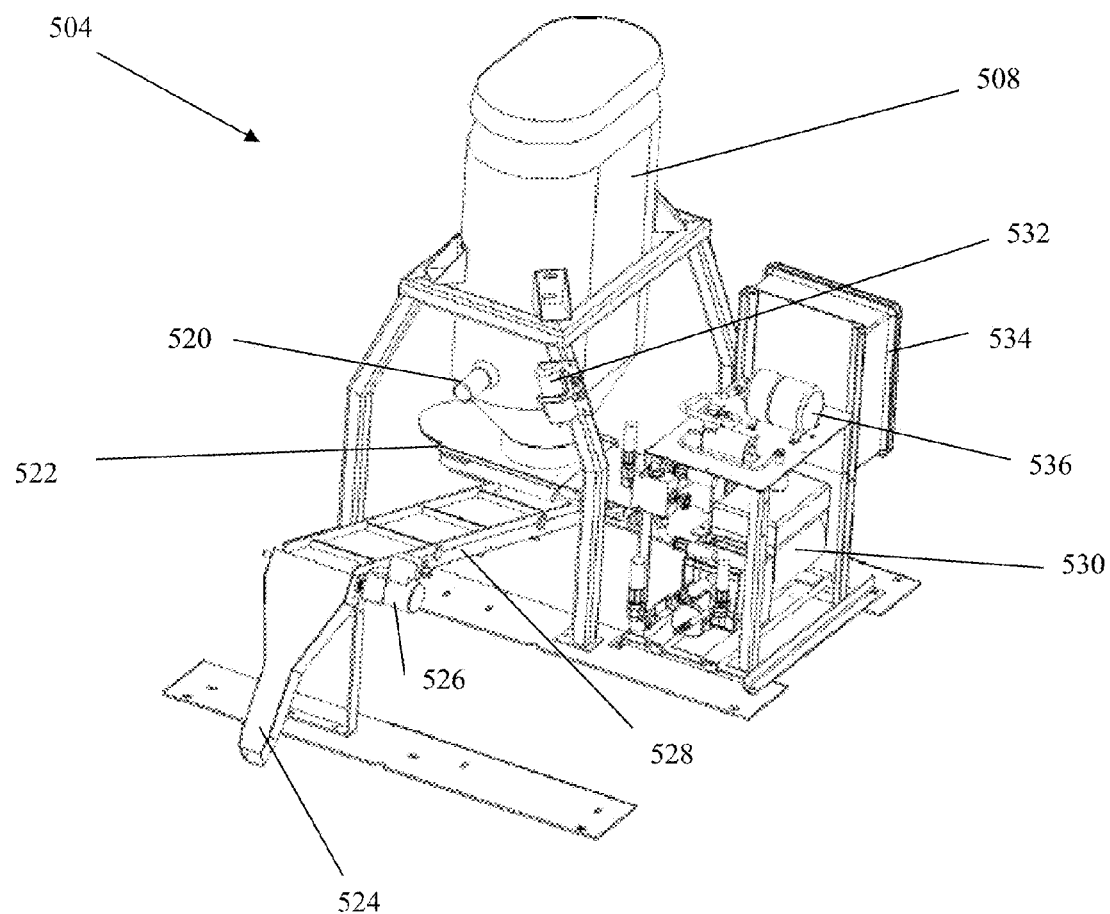
FIG. 9 shows a perspective view of the sample handling system of FIG. 5.

FIG. 9 shows the sample handling system of FIG. 5. The sample handling system 504 can be mounted to the soil sampling machine 500 by any suitable connection technique. The sample handling system 504 can include a vacuum silo or storage tank 508 to store the sample material obtained from the sampling mechanism 502. The vacuum silo or storage tank 508 can include one or more vacuum generators, pumps or motors positioned inside the vacuum silo or tank 508 to generate the vacuum force to transport the sample material from the sampling mechanism 502 to the storage tank 508. The storage tank 508 can have a connection point 520 for the hose connected to the sampling mechanism 502. When sufficient sample material has been collected for a sample, a valve 522 can be opened and the sample material can travel by gravity to a conveyor 528. To assist in removing and loosening the sample material in the storage tank 508, a vibrator or vibrating device 532 can be used on the storage tank 508. A motor 526 can drive the conveyor 528 to enable the conveyor to transport the sample material from the storage tank 508 to a funnel, channel, or passageway 524. The opposite end of the funnel 524 can be located inside the cab of the soil sampling machine 500 to permit the operator to store the sample material in a container or bag. The sample handling system 504 can have a hydraulic generator 530 to provide power to the components of the sampling mechanism 502 and the sample handling system 504 and an air compressor 536. The sample handling system 504 can also include a control panel and/or user interface 534 that can be accessed by the operator and configured to provide control instructions to the components of the sampling mechanism 502 and the sample handling system 504.

Figure 10:
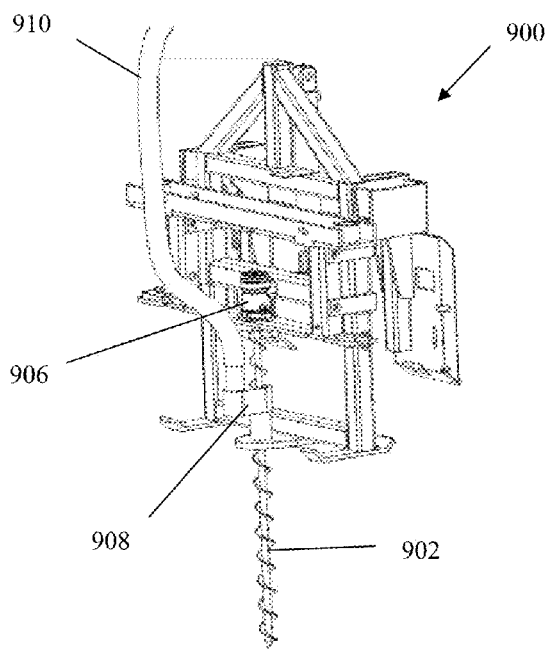
FIGS. 10 and 11 show front and rear views of another exemplary embodiment of a sampling mechanism.
Figure 11:
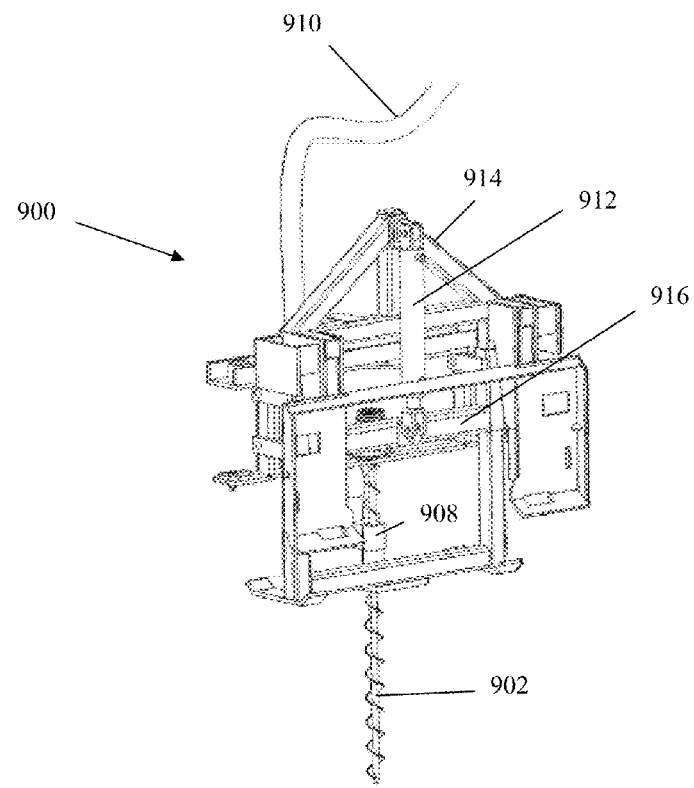

FIGS. 10 and 11 show another exemplary embodiment of a sampling mechanism. A sampling mechanism 900 can be mounted to a soil sampling machine by hydraulic cylinders or other suitable connection techniques. The sampling mechanism 900 can use an auger 902 to acquire the sample material instead of a probe. The auger 902 can be rotated by a motor 906 to transport the sample material along the helical blade of the auger 902 to a storage area 908 that receives and stores the sample material transported by the auger 902. The storage area 908 can include a connection point for the hose 910. The sampling mechanism 900 can also include a hydraulic cylinder 912 mounted on a frame 914 to move a sliding mechanism 916 to which the auger 902 and motor 906 are connected. To acquire sample material with the auger 902, the sampling mechanism 900 is lowered to or positioned onto the ground by the soil sampling machine. Once the sampling mechanism 900 is in the proper position, the hydraulic cylinder 912 can be actuated to move or lower the sliding mechanism 916 along the frame 914 and force the rotating auger 902 into the ground to acquire the sample material. To remove the rotating auger 902 from the ground, the hydraulic cylinder 912 is actuated in the opposite direction to move or raise the sliding mechanism 916 and the auger 902. The movement of the sliding mechanism 916 as well as the configuration of the auger 902 can be used to determine the measurement depth for the auger 902. In an exemplary embodiment, pneumatic cylinders could be used instead of hydraulic cylinders.

In one exemplary embodiment, the process for acquiring a soil sample begins with the operator engaging an auto operation switch in the soil sampling machine. The operator can lower a mast of the soil sampling machine (i.e., position the sampling device on the ground) and then lower the probe (i.e., insert the probe into the ground) to collect the sample material. Once the probe is in the "full up" position, the silo or storage tank vacuum and the front probe vibrator can operate for 5-8 seconds and turn off automatically. The cycle time for the silo vacuum and the front probe vibrator can be programmable by the operator. The silo vacuum system can use one or more high powered motors to generate over 210 CFM of air flow and a vacuum of over 150 inches of water lift. The sample can then be vacuumed from the front probe through a clear collection hose, and deposited into the silo vacuum chamber. When there is enough dirt or soil to make a complete sample (1-2 samples for a 12 inch probe, 2-3 samples for an 8 inch probe and 3-4 samples for a 6 inch probe), the operator can engage a bagging switch. The silo vibrator and the electronic filter shaker can run for 10 seconds and then will turn off automatically. The cycle time for the silo vibrator and the electronic filter shaker can be programmable by the operator. An 8 inch belt conveyor can turn on and the sample can be discharged via an 8 inch air gate and travel up the conveyor, discharge into a stainless steel funnel, and down into a bag located inside the cab. During the bagging operation, the air gate can close in 5 seconds and the conveyor can turn off in 22 seconds after the bagging switch is engaged. The cycle time for the air gate and the conveyor can be programmable by the operator.

In another exemplary embodiment, the soil sampling machine can be built on a 5600 Bobcat® Toolcat™ All Purpose Chassis with a Kubota® 59 hp hydrostatic transmission and can be a 18.9 GPM hydraulic system. The soil sampling machine can include a sampling device with: a 14 inch slide rack and cylinder; a 1.5 inch diameter stainless steel probe, 6 to 12 inches long; a 12 volt, 85 lb. vibrator; a 2.5 inch diameter×14 inch cylinder; and a quick detach capability using hydraulic couplers. The soil sampling machine can also include a silo vacuum with: two (2) 1600 watt, 4.8 hp, 220 volt motors located inside the silo that can operate at a 72 dBa noise level, generate an 11 Hg inch vacuum rating (150 inches of water lift) and generate a 210 CFM volume rating; a primary filter having 13 square feet of area; a heavy duty electric primary filter cleaning shaker; a 2 inch (51 mm) inlet with aluminum cast deflector; a compression housing cast composite; an 8 inch air tight slide gate valve with electric over air activation for sample discharge; and a 12 volt, 85 lb vibrator. The soil sampling machine can include a hydraulic generator with a Hydro 500 hydraulic generator that can provide 5000 (5500 peak) watts of continuous output. The soil sampling machine can include a conveyor with: a 5 foot mini belt conveyor with a 220 volt motor that can operate at 22 feet per minute and has an 8 inch urethane belt with 0.80 inch cleats every 12 inches; aluminum side rails; and a stainless steel hopper with bagging tube and bag holder. The soil sampling machine can include an air compressor with: a storage tank; 110 psi output; a 12 volt motor; a built-in regulator that can turn on the air compressor at 85 psi and turn off the air compressor at 110 psi; and 20 feet of ¼ inch air hose.

In other exemplary embodiment, the soil sampling machine can include agricultural management software such as AgJunction®. The agricultural management software can include: a 7 inch touch screen; a 10 Hz DGPS using EGNOSS/WAAS correction; a built-in terrain correction capability; soil sampling, area measurement and record keeping functionality; a guidance mode; a work order system; and an integrated advanced cellular modem for wireless data transfer and logistics.

In one exemplary embodiment, the results from the sampling process can be used to generate soil maps that can then be used to develop prescription or application plans for the agricultural field.

Although the figures herein may show a specific order of method steps, the order of the steps may differ from what is depicted. Also, two or more steps may be performed concurrently or with partial concurrence. Variations in step performance can depend on the systems chosen and on designer choice. All such variations are within the scope of the application.

While the exemplary embodiments illustrated in the figures and described herein are presently preferred, it should be understood that these embodiments are offered by way of example only. Other substitutions, modifications, changes and omissions may be made in the design, operating conditions and arrangement of the exemplary embodiments without departing from the scope of the present application. Accordingly, the present application is not limited to a particular embodiment, but extends to various modifications that nevertheless fall within the scope of the appended claims. It should also be understood that the phraseology and terminology employed herein is for the purpose of description only and should not be regarded as limiting.

It is important to note that the construction and arrangement of the present application as shown in the various exemplary embodiments is illustrative only. Only certain features and embodiments of the invention have been shown and described in the application and many modifications and changes may occur to those skilled in the art (e.g., variations in sizes, dimensions, structures, shapes and proportions of the various elements, values of parameters (e.g., temperatures, pressures, etc.), mounting arrangements, use of materials, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A method of obtaining a soil sample from an agricultural field comprising:
    acquiring sample material from an agricultural field with a sampling mechanism mounted on a soil sampling machine;
    transferring the acquired sample material from the sampling mechanism to a storage tank located on the soil sampling machine with a vacuum force;
    determining whether the acquired sample material in the storage tank is sufficient for a soil sample;
    repeating acquiring sample material, transferring the acquired sample material, and determining whether the acquired sample material in the storage tank is sufficient for a soil sample in response to a determination that the acquired sample material in the storage tank is not sufficient for a soil sample;
    removing the acquired sample material from the storage tank; and
    placing the acquired sample material in a container.

2. The method of claim 1 wherein removing the acquired sample material comprises opening a valve in the storage tank.

3. The method of claim 2 wherein placing the acquired sample material in a container comprises transporting the acquired sample material from the storage tank to the container with a conveyor.

4. The method of claim 1 wherein acquiring sample material from an agricultural field comprises using a probe to obtain soil from the agricultural field.

5. The method of claim 1 wherein acquiring sample material from an agricultural field comprises using an auger to obtain soil from the agricultural field.

6. A method of obtaining a soil sample from an agricultural field comprising:
   acquiring sample material from an agricultural field with a sampling mechanism mounted on a soil sampling machine;
   transferring the acquired sample material from the sampling mechanism to a storage tank located on the soil sampling machine with a vacuum force, wherein transferring the acquired sample material comprises vibrating the sampling mechanism;
   removing the acquired sample material from the storage tank; and
   placing the acquired sample material in a container.

7. A method of obtaining a soil sample from an agricultural field comprising:
   acquiring sample material from an agricultural field with a sampling mechanism mounted on a soil sampling machine;
   transferring the acquired sample material from the sampling mechanism to a storage tank located on the soil sampling machine with a vacuum force;
   removing the acquired sample material from the storage tank, wherein removing the acquired sample material from the storage tank comprises vibrating the storage tank; and
   placing the acquired sample material in a container.

8. A soil sampling machine comprising:
   a sampling mechanism configured and positioned to obtain a soil sample, the sampling mechanism comprising a vibrator to loosen the obtained soil sample from the sampling mechanism;
   a storage tank to store an obtained soil sample from the sampling mechanism;
   a hose connecting the sampling mechanism and the storage tank; and
   a vacuum generator to generate a vacuum force to transport the soil sample from the sampling mechanism to the storage tank.

9. The soil sampling machine of claim 8 wherein the sampling mechanism comprises at least one probe.

10. The soil sampling machine of claim 8 wherein the sampling mechanism comprises an auger.

11. The soil sampling machine of claim 8 further comprising a conveyor to transport the obtained soil sample from the storage tank to a container.

12. The soil sampling machine of claim 11 wherein the storage tank comprises a valve, the valve having an open position to permit the obtained soil sample to travel from the storage tank to the conveyor and a closed position to prevent the obtained soil sample from exiting the storage tank.

13. The soil sampling machine of claim 11 further comprising a funnel having a first end to receive the obtained soil sample from the conveyor and a second end opposite the first end configured to place the obtained soil sample in the container.

14. The soil sampling machine of claim 13 wherein the second end of the funnel is positioned adjacent to an operator of the soil sampling machine.

15. The soil sampling machine of claim 8 wherein the hose comprises a clear tube.

16. The soil sampling machine of claim 8 further comprising a hydraulic generator to provide power to the vacuum generator.

17. A soil sampling machine comprising:
   a sampling mechanism configured and positioned to obtain a soil sample;
   a storage tank to store an obtained soil sample from the sampling mechanism, the storage tank comprising a vibrator to loosen the obtained soil sample from the storage tank;
   a hose connecting the sampling mechanism and the storage tank; and
   a vacuum generator to generate a vacuum force to transport the soil sample from the sampling mechanism to the storage tank.

18. The soil sampling machine of claim 17 wherein the sampling mechanism comprises at least one probe.

* * * * *